(12) United States Patent
Li et al.

(10) Patent No.: US 9,913,594 B2
(45) Date of Patent: Mar. 13, 2018

(54) COMPLIANT ELECTRODE FOR EMG ENDOTRACHEAL TUBE

(71) Applicant: MEDTRONIC XOMED, INC, Jacksonville, FL (US)

(72) Inventors: Wenjeng Li, Saint Johns, FL (US); Dwayne S. Yamasaki, St. Augustine, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 649 days.

(21) Appl. No.: 13/826,323

(22) Filed: Mar. 14, 2013

(65) Prior Publication Data
US 2014/0275914 A1 Sep. 18, 2014

(51) Int. Cl.
| | |
|---|---|
| *A61B 5/0492* | (2006.01) |
| *A61N 1/05* | (2006.01) |
| *A61B 5/0488* | (2006.01) |
| *A61B 5/00* | (2006.01) |
| *A61M 16/04* | (2006.01) |
| *A61N 1/36* | (2006.01) |

(52) U.S. Cl.
CPC ........ *A61B 5/0492* (2013.01); *A61B 5/04886* (2013.01); *A61B 5/4836* (2013.01); *A61B 5/6853* (2013.01); *A61B 5/6882* (2013.01); *A61M 16/0434* (2013.01); *A61M 16/0459* (2014.02); *A61N 1/0519* (2013.01); *A61N 1/3601* (2013.01); *A61M 2230/60* (2013.01)

(58) Field of Classification Search
CPC .... A61B 5/0492; A61B 1/0519; A61N 1/0519
USPC ................... 600/373, 380; 607/116
See application file for complete search history.

(56) References Cited

U.S. PATENT DOCUMENTS

| | | | |
|---|---|---|---|
| 1,864,688 A | 6/1932 | Frank | |
| 2,107,835 A | 2/1938 | Pierce | |
| 2,429,585 A | 10/1947 | Rogoff | |
| 2,618,684 A | 11/1952 | Bergan | |
| 2,872,505 A | 2/1959 | Ustin | |

(Continued)

FOREIGN PATENT DOCUMENTS

| | | |
|---|---|---|
| CN | 2056003 | 4/1990 |
| CN | 2232257 | 8/1996 |

(Continued)

OTHER PUBLICATIONS

"Applications of High-Pressure Balloons in the Medical Device Industry", 1999 Advanced Polymers, Inc. 1999, Mark A. Saab, President (19 pages).

(Continued)

*Primary Examiner* — Lee S Cohen
(74) *Attorney, Agent, or Firm* — Jeffrey J. Hohenshell

(57) ABSTRACT

An apparatus for monitoring EMG signals of a patient's laryngeal muscles includes an endotracheal tube having a first cuff and a second cuff. Conductive ink electrodes are formed on an exterior surface of the first cuff. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

19 Claims, 3 Drawing Sheets

(56) References Cited

U.S. PATENT DOCUMENTS

| | | |
|---|---|---|
| 3,165,575 A | 1/1965 | Lynch, Jr. et al. |
| 3,494,364 A | 2/1970 | Peters |
| 3,734,094 A | 5/1973 | Calinog |
| 3,783,178 A | 1/1974 | Philibert et al. |
| 3,892,455 A | 7/1975 | Sotolongo |
| 3,951,136 A | 4/1976 | Wall |
| 4,090,518 A | 5/1978 | Elam |
| 4,176,660 A | 12/1979 | Mylrea et al. |
| 4,231,365 A | 11/1980 | Scarberry |
| 4,304,239 A | 12/1981 | Perlin |
| 4,349,031 A | 9/1982 | Perlin |
| 4,369,794 A | 1/1983 | Furler |
| 4,461,304 A | 7/1984 | Kuperstein |
| 4,647,713 A | 3/1987 | de Nijis et al. |
| 4,776,808 A | 10/1988 | Davidson |
| 4,836,214 A | 6/1989 | Sramek |
| 4,863,390 A | 9/1989 | Cera et al. |
| 4,890,623 A | 1/1990 | Cook et al. |
| 4,906,244 A | 3/1990 | Pinchuk et al. |
| 4,960,133 A | 10/1990 | Hewson |
| 4,967,759 A | 11/1990 | Teves |
| 5,024,228 A | 6/1991 | Goldstone et al. |
| 5,096,445 A | 3/1992 | Lostumo |
| 5,125,406 A | 6/1992 | Goldstone et al. |
| 5,135,001 A | 8/1992 | Sinofsky et al. |
| 5,170,803 A | 12/1992 | Hewson et al. |
| 5,286,211 A | 2/1994 | McIntosh |
| 5,364,281 A | 11/1994 | Leto |
| 5,379,765 A | 1/1995 | Kajiwara et al. |
| 5,429,617 A | 7/1995 | Hammersmark |
| 5,464,404 A | 11/1995 | Abela et al. |
| 5,554,176 A | 9/1996 | Maddison et al. |
| 5,584,290 A | 12/1996 | Brain |
| 5,672,065 A | 9/1997 | Womack |
| 5,782,744 A | 7/1998 | Money |
| 5,782,774 A | 7/1998 | Shmulewitz |
| 5,785,051 A | 7/1998 | Lipscher et al. |
| 5,836,874 A | 11/1998 | Swanson et al. |
| 5,864,093 A | 1/1999 | Hecock et al. |
| 5,924,984 A | 7/1999 | Rao |
| 5,972,026 A | 10/1999 | Laufer et al. |
| 6,010,500 A | 1/2000 | Sherman et al. |
| 6,032,065 A | 2/2000 | Brown |
| 6,062,223 A | 5/2000 | Palazzo et al. |
| 6,095,987 A | 8/2000 | Shmulewitz et al. |
| 6,142,993 A | 11/2000 | Whayne et al. |
| 6,148,222 A | 11/2000 | Ramsey, III |
| 6,226,548 B1 | 5/2001 | Foley et al. |
| 6,259,938 B1 | 7/2001 | Zarychta et al. |
| 6,266,548 B1 | 7/2001 | Lamade et al. |
| 6,266,549 B1 | 7/2001 | Melnikoff et al. |
| 6,292,701 B1 | 9/2001 | Prass et al. |
| 6,334,068 B1 | 12/2001 | Hacker |
| 6,343,233 B1 | 1/2002 | Werner et al. |
| 6,357,447 B1 | 3/2002 | Swanson et al. |
| 6,443,156 B1 | 9/2002 | Niklason et al. |
| 6,547,788 B1 | 4/2003 | Maguire et al. |
| 6,584,347 B1 | 6/2003 | Sinderby |
| 6,626,841 B1 | 9/2003 | Atlee, III |
| 6,626,899 B2 | 9/2003 | Houser et al. |
| 6,735,471 B2 | 5/2004 | Hill et al. |
| 6,869,431 B2 | 3/2005 | Maguire et al. |
| 6,877,512 B2 | 4/2005 | Imai et al. |
| 6,976,857 B1 | 12/2005 | Shukla |
| 7,008,419 B2 | 3/2006 | Shadduck |
| 7,146,222 B2 | 12/2006 | Boling |
| 7,153,146 B2 | 12/2006 | Shimizu et al. |
| 7,179,345 B2 | 2/2007 | Shkolnik |
| 7,216,001 B2 | 5/2007 | Hacker et al. |
| 7,293,562 B2 | 11/2007 | Malecki et al. |
| 7,507,239 B2 | 3/2009 | Shadduck |
| 7,583,991 B2 | 9/2009 | Rea |
| 7,736,362 B2 | 6/2010 | Eberl et al. |
| 7,794,256 B1 | 9/2010 | Sochor |
| 7,972,308 B2 | 7/2011 | Putz |
| 8,145,289 B2 | 3/2012 | Calabro' et al. |
| 8,152,803 B2 | 4/2012 | Edwards et al. |
| 8,224,422 B2 | 7/2012 | Mottola et al. |
| 8,352,012 B2 | 1/2013 | Besio |
| 8,467,844 B2 | 6/2013 | Rea et al. |
| 8,634,894 B2 | 1/2014 | Rea et al. |
| 8,688,237 B2 | 4/2014 | Stanislaus et al. |
| 8,886,280 B2 | 11/2014 | Kartush |
| 9,037,226 B2 | 5/2015 | Hacker et al. |
| 9,060,744 B2 | 6/2015 | Li |
| 9,289,141 B2 | 3/2016 | Lowery et al. |
| 9,398,865 B2 | 7/2016 | Li |
| 9,763,624 B2 | 9/2017 | Stanislaus et al. |
| 2001/0018281 A1 | 8/2001 | Royer |
| 2002/0016615 A1 | 2/2002 | Dev et al. |
| 2002/0032468 A1 | 3/2002 | Hill et al. |
| 2002/0188332 A1 | 12/2002 | Lurie et al. |
| 2003/0018327 A1 | 1/2003 | Truckai et al. |
| 2003/0074039 A1 | 4/2003 | Puskas |
| 2004/0186461 A1 | 9/2004 | DiMatteo |
| 2004/0230110 A1 | 11/2004 | Sinderby et al. |
| 2005/0085111 A1 | 4/2005 | Clark et al. |
| 2005/0113686 A1 | 5/2005 | Peckham |
| 2005/0159659 A1 | 7/2005 | Sawan et al. |
| 2005/0222656 A1 | 10/2005 | Wahlstrand et al. |
| 2005/0255727 A1 | 11/2005 | Alladice |
| 2006/0012671 A1 | 1/2006 | Nimri et al. |
| 2006/0025702 A1 | 2/2006 | Sterrantino et al. |
| 2006/0116564 A1 | 6/2006 | Mintchev et al. |
| 2006/0241725 A1 | 10/2006 | Libbus et al. |
| 2006/0254595 A1 | 11/2006 | Rea |
| 2007/0074728 A1 | 4/2007 | Rea |
| 2007/0137651 A1 | 6/2007 | Glassenberg et al. |
| 2007/0142888 A1 | 6/2007 | Chavez |
| 2007/0156041 A1 | 7/2007 | Rea |
| 2007/0170928 A1 | 7/2007 | Fedan et al. |
| 2007/0219551 A1 | 9/2007 | Honour et al. |
| 2008/0077043 A1 | 3/2008 | Malbrain et al. |
| 2008/0140052 A1 | 6/2008 | Moller et al. |
| 2008/0177190 A1 | 7/2008 | Libbus et al. |
| 2008/0249507 A1 | 10/2008 | Hadani |
| 2008/0255441 A1 | 10/2008 | Hadani |
| 2008/0300650 A1 | 12/2008 | Gerber et al. |
| 2009/0227885 A1 | 9/2009 | Lowery et al. |
| 2010/0006103 A1 | 1/2010 | McGinnis et al. |
| 2010/0036229 A1 | 2/2010 | Weekamp et al. |
| 2010/0063376 A1 | 3/2010 | Kartush |
| 2010/0087782 A1 | 4/2010 | Ghaffari et al. |
| 2010/0145178 A1 | 6/2010 | Kartush |
| 2010/0168561 A1 | 7/2010 | Anderson |
| 2010/0168743 A1 | 7/2010 | Stone et al. |
| 2010/0179417 A1 | 7/2010 | Russo |
| 2010/0191311 A1 | 7/2010 | Scheiner |
| 2010/0198099 A1 | 8/2010 | Murphy et al. |
| 2010/0317956 A1 | 12/2010 | Kartush |
| 2011/0023889 A1 | 2/2011 | Lin et al. |
| 2011/0030694 A1 | 2/2011 | Schaner et al. |
| 2011/0071379 A1 | 3/2011 | Rea et al. |
| 2011/0190596 A1 | 8/2011 | Hacker et al. |
| 2011/0230734 A1 | 9/2011 | Fain et al. |
| 2011/0245647 A1 | 10/2011 | Stanislaus et al. |
| 2011/0301587 A1 | 12/2011 | Deem et al. |
| 2011/0306861 A1 | 12/2011 | Thramann et al. |
| 2012/0016256 A1 | 1/2012 | Mabary et al. |
| 2012/0024292 A1 | 2/2012 | Sandmore et al. |
| 2012/0055257 A1 | 3/2012 | Shaw-Klein |
| 2013/0172714 A1 | 7/2013 | Li et al. |
| 2014/0148672 A1* | 5/2014 | Li .................. 600/373 |
| 2014/0155720 A1 | 6/2014 | Stanislaus et al. |
| 2015/0250423 A1 | 9/2015 | Hacker et al. |
| 2016/0038072 A1 | 2/2016 | Brown et al. |
| 2016/0038073 A1 | 2/2016 | Brown et al. |
| 2016/0038074 A1 | 2/2016 | Brown et al. |
| 2016/0262699 A1 | 9/2016 | Goldstone et al. |
| 2016/0287112 A1 | 10/2016 | McFarlin et al. |
| 2016/0287861 A1 | 10/2016 | McFarlin et al. |
| 2016/0324475 A1 | 11/2016 | Hacker |
| 2016/0345905 A1 | 12/2016 | Li |
| 2017/0007146 A1 | 1/2017 | Schulhauser et al. |

(56) References Cited

U.S. PATENT DOCUMENTS

FOREIGN PATENT DOCUMENTS

| | | |
|---|---|---|
| CN | 2827273 | 10/2006 |
| DE | 29715344 | 1/1988 |
| DE | 29715344 | 1/1998 |
| DE | 19750705 | 3/2000 |
| EP | 0438863 | 11/1990 |
| EP | 1750368 A1 | 2/2007 |
| GB | 1214718 | 12/1970 |
| JP | H03-182230 | 8/1991 |
| JP | 2001-224554 | 8/2001 |
| JP | 2003-019200 | 1/2003 |
| JP | 2003-527164 | 9/2003 |
| JP | 2006-528890 | 12/2006 |
| JP | 2007-307185 | 11/2007 |
| JP | 2007-532152 | 11/2007 |
| JP | 2009-519763 | 5/2009 |
| JP | 2009-524482 | 7/2009 |
| KR | 1020060031799 | 4/2006 |
| WO | 199723163 | 7/1997 |
| WO | 200141638 | 6/2001 |
| WO | 2004/100786 | 11/2004 |
| WO | 2005/097246 | 10/2005 |
| WO | 2006012671 | 2/2006 |
| WO | 2006012672 | 2/2006 |
| WO | 2007/078827 | 7/2007 |
| WO | 2007/089491 | 8/2007 |
| WO | 2008/091928 | 7/2008 |
| WO | 2011/041690 | 4/2011 |
| WO | 2011041690 | 4/2011 |
| WO | 2013/008106 | 1/2013 |

OTHER PUBLICATIONS

PCT Search Report and Written Opinion, PCT/US2014/027810, date of mailing Jul. 25, 2014, 18 pages.
Restriction Requirement for U.S. Appl. No. 12/896,578 dated Jul. 24, 2012 (8 pages).
Non-Final Office Action for U.S. Appl. No. 12/896,578 dated Oct. 3, 2012 (16 pages).
Non-Final Office Action for U.S. Appl. No. 12/896,578 dated Sep. 19, 2013 (16 pages).
Notice of Allowance for U.S. Appl. No. 12/896,578 dated Feb. 27, 2014 (7 pages).
Notice of Allowance for U.S. Appl. No. 12/896,578 dated Jun. 9, 2014 (11 pages).
Notice of Allowance for U.S. Appl. No. 12/896,578 dated Aug. 5, 2014 (12 pages).
Notice of Allowance for U.S. Appl. No. 12/896,578 dated Oct. 6, 2014 (11 pages).
Notice of Allowance for U.S. Appl. No. 12/896,578 dated Jan. 28, 2015 (12 pages).
Notice of Allowance for U.S. Appl. No. 12/896,578 dated Mar. 30, 2015 (11 pages).
PCT Search Report dated Apr. 28, 2011 for PCT/US2010/051132 (17 pages).
International Preliminary Report on Patentability for PCT/US2010/051132, dated Dec. 5, 2011 (5 pages).
Australian Examination Report dated Feb. 25, 2013 (4 pages) re 2010300373.
Canadian 1st Examiner's Report for 2775588 dated Oct. 28, 2016 (4 pages). (.211).
Chinese 1st Office Action for 201080054559.2 dated Feb. 14, 2014 (5 pages).
Chinese 2nd Office Action for Application No. 201080054559.2, dated Jul. 17, 2014 (10 pages).
Japanese Office Action for Application No. 2012/532,355, dated Apr. 18, 2014 (7 pages).
European Examination Report for Application No. 10781544.1, dated Feb. 19, 2014 (4 pages). (.291).
Extended European Search Report for Serial No. 14182496.1, dated Nov. 28, 2014 (7 pages). (.292).
Korean 1st Office Action for 10-2012-7011251 dated Feb. 6, 2017 (13 pages).
Restriction Requirement for U.S. Appl. No. 14/716,351 dated Jan. 22, 2016 (5 pages).
Non-Final Office Action for U.S. Appl. No. 14/716,351 dated May 3, 2016 (25 pages).
Non-Final Office Action for U.S. Appl. No. 14/716,351 dated Sep. 21, 2016 (6 pages).
Final Office Action for U.S. Appl. No. 14/716,351 dated Mar. 21, 2017 (30 pages).
Non-Final Office Action for U.S. Appl. No. 14/716,351 dated May 17, 2017 (13 pages).
Non-Final Office Action for U.S. Appl. No. 12/896,593 dated Sep. 5, 2012 (17 pages).
Final Office Action for U.S. Appl. No. 12/896,593, dated Jan. 3, 2013 (13 pages).
Advisory Action for U.S. Appl. No. 12/896,593 dated Apr. 10, 2013 (7 pages).
Notice of Allowance for U.S. Appl. No. 12/896,593 dated Aug. 15, 2013 (11 pages).
Notice of Allowance for U.S. Appl. No. 12/896,593 dated Nov. 7, 2013 (13 pages).
PCT Search Report dated Feb. 4, 2011 for PCT/US2010/051145 (15 pages).
International Preliminary Report on Patentability dated Oct. 24, 2011 for PCT/US2010/051145 (12 pages).
Australian Examination Report No. 1 for Application No. 2010300379, dated May 30, 2014 (4 pages). (.141).
Australian Examination Report No. 1 for Application No. 2015200049, dated Mar. 10, 2016 (3 pages). (.142).
Canadian 1st Examiner's Report for 2776163 dated Oct. 28, 2016 (4 pages). (.211).
Chinese 1st Office Action for 201080054850.X dated Feb. 20, 2014 (19 pages).
Chinese 2nd Office Action for Application No. 201080054850.X, dated Jul. 23, 2014 (6 pages).
European Examination Report for Application No. 10779358.0, dated Feb. 19, 2014 (4 pages). (.291).
Extended European Search Report for Application No. 16176750.4, dated Nov. 22, 2016 (6 pages). (.292).
Japanese Office Action for Application No. 2012/532,356, dated Apr. 18, 2014 (7 pages).
Japanese Office Action for Application No. 2014/189873, dated Aug. 30, 2015 (5 pgs) (.442).
Notice of Allowance for U.S. Appl. No. 14/175,165 dated May 29, 2014 (28 pages).
Non-Final Office Action for U.S. Appl. No. 14/175,165, dated Aug. 15, 2014 (17 pages).
Final Office Action for U.S. Appl. No. 14/175,165, dated Dec. 4, 2014 (13 pages).
Non-Final Office Action for U.S. Appl. No. 14/175,165, dated Mar. 3, 2015 (12 pages).
Final Office Action for U.S. Appl. No. 14/175,165, dated Jun. 12, 2015 (16 pages).
Advisory Action for U.S. Appl. No. 14/175,165, dated Sep. 25, 2015 (6 pages).
Non-Final Office Action for U.S. Appl. No. 14/175,165 dated Jan. 5, 2016 (22 pages).
Final Office Action for U.S. Appl. No. 14/175,165 dated May 19, 2016 (24 pages).
Notice of Allowance for U.S. Appl. No. 14/175,165 dated Feb. 23, 2017 (13 pages).
Corrected Notice of Allowability for U.S. Appl. No. 14/175,165 dated Mar. 23, 2017 (18 pages).
Notice of Allowance for U.S. Appl. No. 14/175,165 dated May 22, 2017 (12 pages).
U.S. Appl. No. 15/217,572, filed Jul. 22, 2016, Inventor: David C. Hacker (65 pages).
Non-Final Office Action for U.S. Appl. No. 15/217,572 dated Feb. 9, 2017 (13 pages).

(56) References Cited

OTHER PUBLICATIONS

Final Office Action for U.S. Appl. No. 15/217,572 dated Jun. 6, 2017 (22 pages).
Non-Final Office Action for U.S. Appl. No. 13/343,283, dated Oct. 2, 2014 (26 pages).
Final Office Action for U.S. Appl. No. 13/343,283, dated May 26, 2015 (18 pages).
Advisory Action for U.S. Appl. No. 13/343,283, dated Aug. 28, 2015 (4 pages).
Non-Final Office Action for U.S. Appl. No. 13/343,283, dated Jan. 13, 2016 (19 pages).
Final Office Action for U.S. Appl. No. 13/343,283 dated Jul. 15, 2016 (22 pages).
Advisory Action for U.S. Appl. No. 13/343,283 dated Sep. 26, 2016 (4 pages).
Office Action for U.S. Appl. No. 13/343,283 dated Jan. 6, 2017 (24 pages).
Electric Motion Company, webpage "Telephony & CATV Products [Bronze Vise Type Connectors]" published Aug. 19, 2007, retrieved via Wayback Machine Jun. 20, 2016 (11 pages).
Southern Grounding Products, webpage "Grounding & ground Rod Clamps" published Nov. 19, 2008, retrieved via Wayback Machine Jun. 20, 2016 (5 pages).
Australian 1st Examination Report for 2012363699 dated Sep. 8, 2016 (3 pages). (.141).
Chinese 1st Office Action for 201280071074.3 dated Oct. 30, 2015 (12 pages). (.231).
Japanese 1st Office Action for 2014-551252 dated Oct. 20, 2016 (3 pages). (.441).
Australian 2nd Examination Report for 2012363699 dated Jun. 22, 2017 (6 pages). (.141).
Non-Final Office Action for U.S. Appl. No. 13/688,818 dated Mar. 13, 2014 (10 pages).
Final Office Action for U.S. Appl. No. 13/688,818 dated Jun. 25, 2014 (10 pages).
Non-Final Office Action for U.S. Appl. No. 13/688,818 dated Oct. 9, 2014 (7 pages).
Notice of Allowance for U.S. Appl. No. 13/688,818 dated Feb. 20, 2015 (7 pages).
International Search Report and Written Opinion, PCT/US2013/072193, dated Mar. 11, 2014 (18 pages).
Australian 1st Examination Report for 2013406220 dated May 19, 2016 (3 pages). (.141).
Non-Final Office Action for U.S. Appl. No. 14/747,257 dated Nov. 17, 2015 (10 pages).
Notice of Allowance for U.S. Appl. No. 14/747,257 dated Mar. 23, 2016 (5 pages).
Final Office Action for U.S. Appl. No. 15/219,726 dated Oct. 21, 2016 (34 pages).
Advisory Action for U.S. Appl. No. 15/219,726 dated Jan. 5, 2017 (4 pages).
Non-Final Office Action for U.S. Appl. No. 15/219,726 dated Apr. 11, 2017 (23 pages).
European Office Action for Application No. 14720826.8, dated Aug. 2, 2016 (8 pgs).
European Office Action for Application No. 14720826.8, dated Feb. 1, 2017 (6 pgs).
Defendants' Invalidity Contentions and Document Production Pursuant to Patent Local Rules 3-3 and 3-4; *Neurovision Medical Products, Inc.* v. *Medtronic Public Limited Company, Medtronic, Inc.; Medtronic Xomed, Inc. HCA Holdings, Inc.; and Healthtrust Purchasing Group, L.P.*; Civ. No. 2:16-cv-00127-JRP-RSP, signed by James M. Hilmert, dated Jun. 10, 2016 (147 pages).
Hon, Li & Hutchings, "Direct writing technology—Advances and developments," CIRP Annals—Manufacturing Technology, vol. 57, Issue 2, presented on Aug. 25, 2008 and published Oct. 28, 2008, pp. 601-620 (20 pages).
Kartush et al., "Intraoperative Facial Nerve Monitoring," Ch. 5, Neuromonitoring in Otology and Head and Neck Surgery, Raven Press, Ltd., p. 99-120 (1992) (22 pages).
Goldstone A., Schettino R., "The Electrode Endotracheal Tube: A State of the Art Method for Monitoring the Recurrent Laryngeal Nerve-Vocal Cord Muscle Integrity in the Intubated Patient," presented to the American Academy of Otolaryngology/Head & Neck Surgery Annual National Meeting, San Diego, CA. (Sep. 1990) (1 page).
Eisele D.W., Goldstone A., "Electrophysiologic Identification and Preservation of the Superior Laryngeal Nerve During Thyroid Surgery," The Laryngescope, vol. 101, Issue 3, pp. 313-315 (Mar. 1991) (3 pages).
Bakhshaee et al., "Evaluation of the Distance Between Anterior Commissure of True Vocal Folds and the First Tracheal Ring and Related Laryngeal Indices in 40 Human Cadavers," J. Voice, vol. 30, No. 2, p. 159, col. 1 (2016) (3 pages).
Sprinzl et al., "Morphometric Measurements of the Cartilaginous Larynx: an Anatomic Correlate of Laryngeal Surgery," Head & Neck, Figs. 3-4, Tables 2-3, p. 743-750 (Dec. 1999) (8 pages).
Witt, Robert L., "Recurrent Laryngeal Nerve Electrophysiologic Monitoring in Thyroid Surgery: The Standard of Care?" J. Voice, vol. 19, No. 3, pp. 497-500 (2005) (4 pages).
Strauss, Christian et al., "Electrophysiological Localization of Motor Areas within the Rhomboid Fossa During Brainstem Surgery," ECoG, OAE and Intraoperative Monitoring: Proceedings of the First International Conference, (D. Höhmann, ed.) pp. 375-378 (Sep. 1992) (10 pages).
Møller, Aage R., "Monitoring and Mapping the Cranial Nerves and the Brainstem," Ch. 13, Neurophysiology in Neurosurgery: A Modem Intraoperative Approach, Academic Press, pp. 291-318 (2002) (36 pages).
Wang et al., "Prognostic Indicators of Unilateral Vocal Fold Paralysis," Archives of Otolaryngology Head Neck Surgery, vol. 134, No. 4, pp. 380-388 (Apr. 2008) (11 pages).
Dimopoulos et al., "Quantitative Estimation of the Recurrent Laryngeal Nerve Irritation by Employing Spontaneous Intraoperative Electromyographic Monitoring During Anterior Cervical Discectomy and Fusion," J. Spinal Disorder Tech, vol. 22, No. 1, pp. 1-7 (Feb. 2009) (7 pages).
Ajmani, M.L., "A Metrical Study of the Laryngeal Skeleton in Adult Nigerians," J. Anat., vol. 171, pp. 187-191 (1990) ("Ajmani Article") (5 pages).
Grillo, Hermes, Surgery of the Trachea and Bronchi, BC Decker Inc., pp. 39-59 (2004) (23 pages).
Livingstone, Churchill, Gray's Anatomy, pp. 1637-1657 (1995) (28 pages).
Special 510(k) Premarket Notification, K094054, Neurovision® EMG Endotracheal Tube dated May 14, 2010 (6 pages).
Pictures of a NuVasive EMG tube (5 pages).
David L. Bourell et al., Solid Freeform Fabrication Proceedings, Aug. 2004, © 2004 The University of Texas at Austin (15 pages).
ECOM™ Brochure for Endotracheal Cardiac Output Monitor, © 2008 ConMed Corporation Sep. 2008 (2 pages).
James K. Brown et al., Parasympathetic Innervation of the Cervical Trachealis Muscle in Living Dogs, © 1982 The American Physiology Society, vol. 53, No. 3, pp. 617-625 (9 pages).
NuVasive® NVJBB® EMG Endotracheal Tube IFU Product Insert (2 pages).
NuVasive® NeuroVision® EMG Endotracheal Tube brochure—© 2010 NuVasive, Inc. (4 pages).
Cahide Topsakal et al., Intraoperative Monitoring of Lower Cranial Nerves in Skull Base Surgery: Technical Report and Review of 123 Monitored Cases, Neurosurg. Rev., vol. 31, pp. 45-52 Published Online Oct. 24, 2007 © Springer-Verlag 2007 (9 pages).
Jasper R. Daube et al., Clinical Neurophysiology, Third Edition, Oxford University Press. Chapters 25, 43 and 44, © 2009 (71 pages).
U.S. Appl. No. 61/244,402, filed Sep. 21, 2009 (11 pages).
U.S. Appl. No. 14/945,167, filed Nov. 18, 2015 (89 pages).
U.S. Appl. No. 14/945,208, filed Nov. 18, 2015 (88 pages).
Affidavit of Christopher Butler with Exhibit A dated Nov. 10, 2016 (8 pages).

(56) References Cited

OTHER PUBLICATIONS

Decision—Institution of Inter Partes Review; *Medtronic Xomed, Inc. v. Neurovision Medical Products, Inc.*; PTAB Case IPR2016-01405; for U.S. Pat. No. 8,634,894 entered Dec. 29, 2016 (35 pages).
Petition for Inter Partes Review; *Medtronic Xomed, Inc. v. Neurovision Medical Products, Inc.*; PTAB Case IPR2017-00456; for U.S. Pat. No. 8,634,894 dated Dec. 9, 2016 (58 pages).
Patentee's Preliminary Response to Petition for Inter Partes Review; *Medtronic Xomed, Inc. v. Neurovision Medical Products, Inc.*; PTAB Case IPR2016-01405; for U.S. Pat. No. 8,634,894 dated Oct. 20, 2016 (74 pages).
Declaration of Mike Lieu—Exhibit 2002 to Patentee's Preliminary Response to Petition for Inter Partes Review dated Oct. 20, 2016 (7 pages).
Declaration of Stephen W. Blakely—Exhibit 2003 to Patentee's Preliminary Response to Petition for Inter Partes Review dated Oct. 20, 2016 (7 pages).
Declaration of James Lee Rea—Exhibit 2004 to Patentee's Preliminary Response to Petition for Inter Partes Review dated Oct. 20, 2016 (6 pages).
Declaration of Ryan M. Rea—Exhibit 2005 to Patentee's Preliminary Response to Petition for Inter Partes Review dated Oct. 20, 2016 (2 pages).
"Thyroid Surgery May Result in Paralysis of Vocal Cords," Wall Street Journal article dated Aug. 10, 2001 to Exhibit 2006 to Patentee's Preliminary Response to Petition for Inter Partes Review dated Oct. 20, 2016 (4 pages).
Medtronic webpage at http://medtronic.com/us-en/healthcare-nim-nerve-monitoring-systems/related-nerve-monitoring-products.html—Exhibit 2007 to Patentee's Preliminary Response to Petition for Inter Partes Review dated Oct. 20, 2016 (5 pages).
Medtronic product recall notice—Exhibit 2008 to Patentee's Preliminary Response to Petition for Inter Partes Review dated Oct. 20, 2016 (4 pages).
MicroPenning: How It Works—Exhibit 2009 to Patentee's Preliminary Response to Petition for Inter Partes Review dated Oct. 20, 2016 (2 pages).
MicroPenning: Overview—Exhibit 2010 to Patentee's Preliminary Response to Petition for Inter Partes Review dated Oct. 20, 2016 (3 pages).
U.S. Pat. No. 4,461,304 to Kuperstein—Exhibit 2011 to Patentee's Preliminary Response to Petition for Inter Partes Review dated Oct. 20, 2016 (10 pages).
U.S. Appl. No. 61/126,567—Exhibit 2012 to Patentee's Preliminary Response to Petition for Inter Partes Review dated Oct. 20, 2016 (8 pages).
NuVasive, Inc.'s Petition for Inter Partes Review file in IPR2015-00502—Exhibit 2014 to Patentee's Preliminary Response to Petition for Inter Partes Review dated Oct. 20, 2016 (63 pages).
PTAB's Decision dated Jul. 16, 2015 in IPR2015-00502—Exhibit 2015 to Patentee's Preliminary Response to Petition for Inter Partes Review dated Oct. 20, 2016 (31 pages).
Table of page cites and summary regarding Exhibit 2001—Exhibit 2016 to Patentee's Preliminary Response to Petition for Inter Partes Review dated Oct. 20, 2016 (14 pages).
Redacted Exhibit 2001—Confidential Neurovision emails regarding conception and reduction to practice—Exhibit 2017 to Patentee's Preliminary Response to Petition for Inter Partes Review dated Oct. 20, 2016 (140 pages).
Decision; *Medtronic Xomed, Inc. v. Neurovision Medical Products, Inc.*; PTAB Case IPR2016-01847; for U.S. Pat. No. 8,467,844 entered Mar. 23, 2017 (37 pages).
Korean Final Office Action for 10-2012-7011251 dated Jun. 28, 2017 (7 pages).
Final Office Action for U.S. Appl. No. 13/343,283 dated Jul. 11, 2017 (24 pages).
Japanese 1st Office Action for 2016-502632 dated Jul. 7, 2017 (8 pages).
Final Office Action for U.S. Appl. No. 15/219,726 dated Aug. 2, 2017 (10 pages).
Australian 1st Examination Report for Application No. 2014236572, dated Aug. 10, 2017 (4 pgs).
Canadian 2nd Examiner's Report for 2775588 dated Sep. 5, 2017 (4 pages).
Notice of Allowance for U.S. Appl. No. 14/716,351 dated Sep. 27, 2017 (11 pages).
Advisory Action for U.S. Appl. No. 15/217,572 dated Sep. 29, 2017 (4 pages).
Notice of Allowance for U.S. Appl. No. 15/217,572 dated Nov. 3, 2017 (10 pages).
Notice of Allowance for U.S. Appl. No. 13/343,283 dated Oct. 12, 2017 (12 pages).
Corrected Notice of Allowability for U.S. Appl. No. 13/343,283 dated Nov. 1, 2017 (15 pages).
Australian 3rd Examination Report for 2012363699 dated Sep. 5, 2017 (3 pages).
International Search Report and Written Opinion, PCT/US2012/069253, dated Feb. 28, 2013 (8 pages).
European Examination Report for Application No. 12818693.9 dated Oct. 25, 2017.
European Office Action for Application No. 13812262.7, dated Aug. 2, 2017 (8 pages).
Notice of Allowance for U.S. Appl. No. 15/219,726 dated Oct. 2, 2017 (8 pages).
European Office Action for Application No. 14720826.8, dated Jul. 17, 2017 (6 pgs).

\* cited by examiner

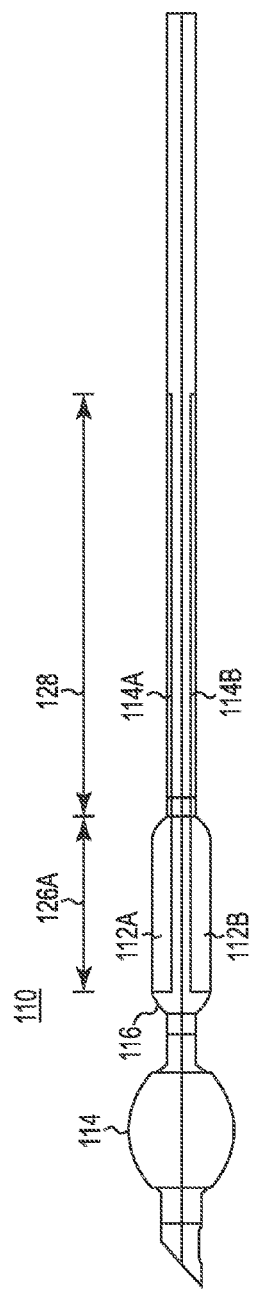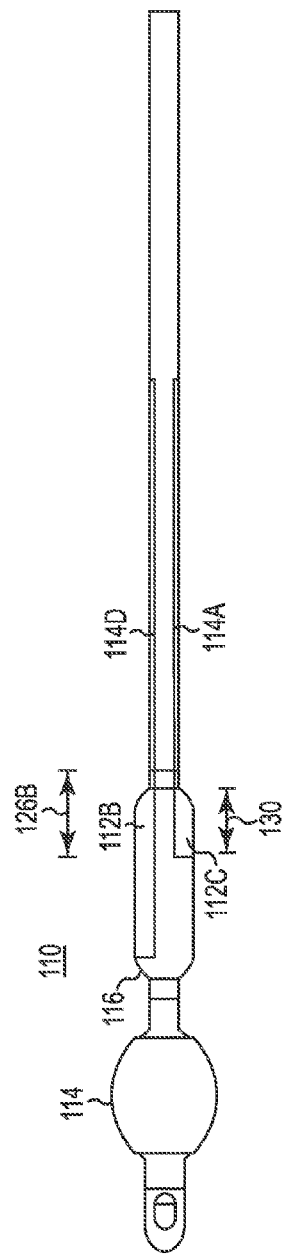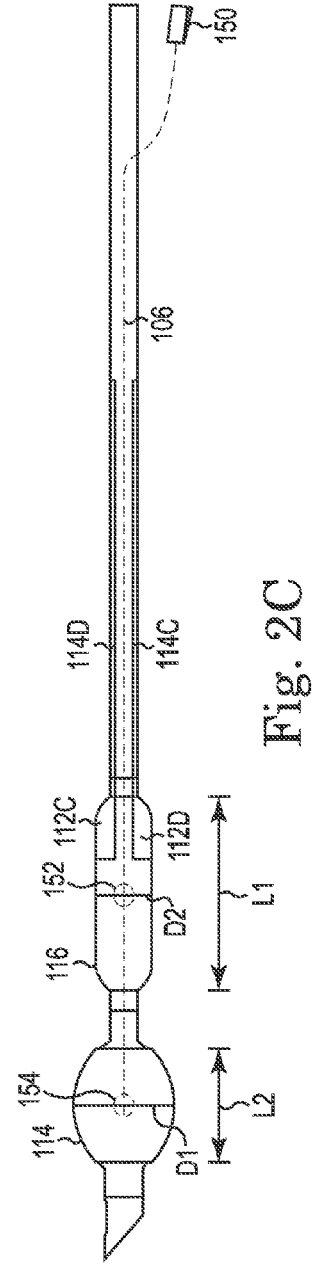

COMPLIANT ELECTRODE FOR EMG ENDOTRACHEAL TUBE

BACKGROUND

Endotracheal tubes include electrodes that are designed to make contact with a patient's vocal cords to facilitate electromyographic (EMG) monitoring of the vocal cords during surgery when connected to an EMG monitoring device. Endotracheal tubes provide an open airway for patient ventilation, and provide for monitoring of EMG activity of the intrinsic laryngeal musculature when connected to an appropriate EMG monitor. Endotracheal tubes can provide, continuous monitoring of the nerves supplying the laryngeal musculature during surgical procedures.

SUMMARY

One embodiment is directed to an apparatus for monitoring EMG signals of a patient's laryngeal muscles. The apparatus includes an endotracheal tube and a conduit extending along the endotracheal tube with two cuffs or balloons. A first cuff has an exterior surface defining a first diameter and is fluidly coupled to the conduit. The first cuff exhibits a first compliance such that the first diameter expands to a first distance when pressurized fluid is within the conduit. A second cuff has an exterior surface defining a second diameter and is positioned distal the first cuff. The second cuff is also fluidly coupled to the conduit. The second cuff exhibits a second compliance that is equal to the first compliance and defined such that the second diameter expands to a second distance greater than the first distance when pressurized fluid is within the conduit. Conductive ink electrodes are formed on the exterior surface of the first cuff. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

Another embodiment is directed to the method of monitoring EMG signals of a patient. The method includes providing a tube having a conduit extending along the tube. An electrode cuff is provided having an exterior surface defining an electrode cuff diameter and an electrode cuff compliance. Conductive electrodes are positioned on the exterior surface of the electrode cuff. Furthermore, the method includes providing a anchoring cuff having an exterior surface defining an anchoring cuff diameter and an anchoring cuff compliance wherein the anchoring cuff compliance is equal to the electrode cuff compliance. Pressurized fluid is provided through the interior conduit to inflate the electrode cuff and the anchoring cuff. Upon inflation, the electrode cuff diameter is less than the anchoring cuff diameter.

BRIEF DESCRIPTION OF THE DRAWINGS

FIGS. 2A-2C are different side views of a tube illustrated in FIG. 1.

DETAILED DESCRIPTION

Figure 1:
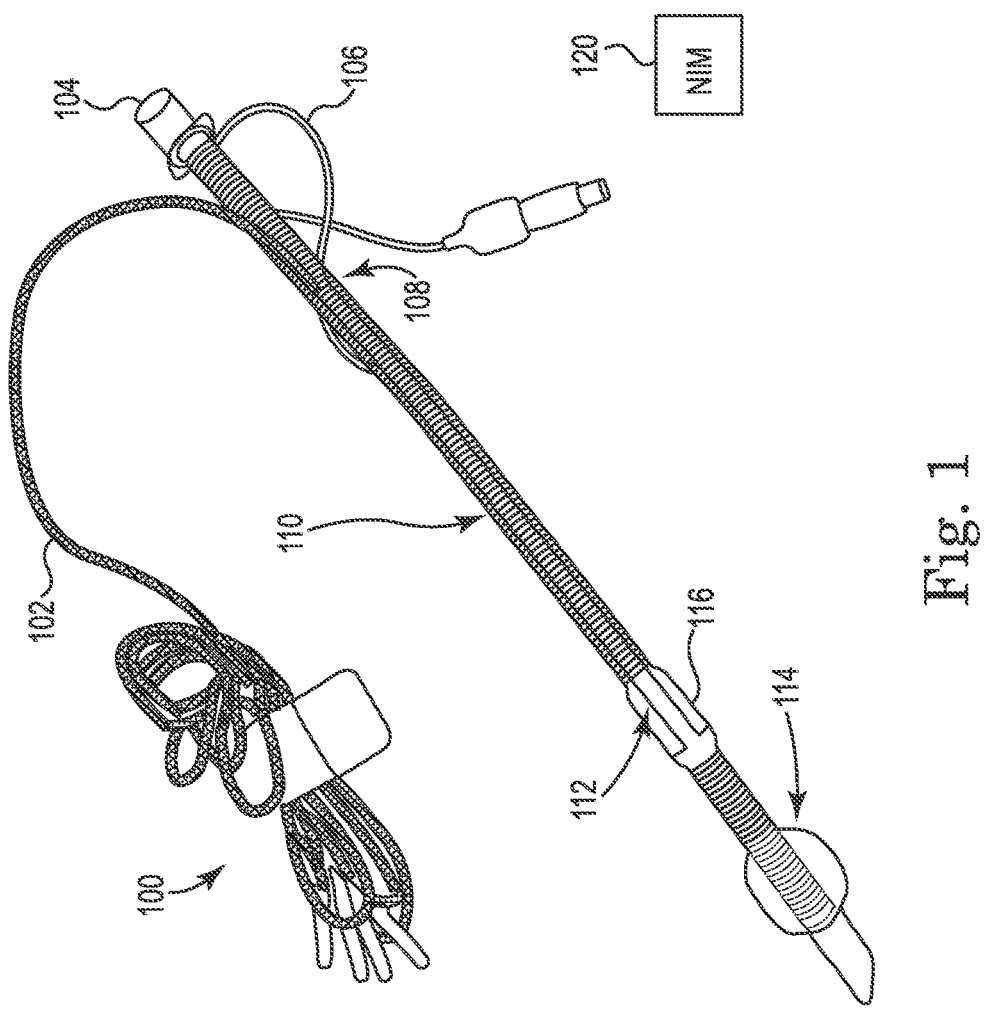
FIG. 1 is an isometric view of an EMG endotracheal tube and nerve monitoring device.

FIG. 1 shows an apparatus embodied as an EMG endotracheal tube 100 made from extruded polymer for monitoring EMG signals of a patient. Endotracheal tube 100 includes wires 102 (e.g., solid, multistranded), fitting 104, cuff inflating conduit 106, extruded polymer tube 110, surface printed electrodes 112, anchoring cuff 114 and electrode cuff 116. Wires 102 are connected to surface printed electrodes 112 located on the electrode cuff 116 at interconnection 108. Tube 110 transports gasses to and from the lungs. Fitting 104 is configured to be connected to a respirating machine (not shown) for injecting air into the lungs and withdrawing air from the lungs. Cuff inflating conduit 106 is configured to be connected to a source of compressed air (not shown) for inflating cuffs 114 and 116. Cuff inflating conduit 106 communicates with a lumen located in the wall of tube 110, and the lumen communicates with anchoring cuff 114 and electrode cuff 116. After endotracheal tube 100 is inserted into the trachea of a patient, surface printed electrodes 112 send EMG signals, which are output to an EMG processing machine, such as the Medtronic Nerve Integrity Monitor (NIM) device 120, via wires 102. Die cut tape may be used to tape tube 110 to a patient's mouth to secure the tube and keep it appropriately positioned.

In one embodiment, the NIM 120 is configured to determine when the electrodes 112 are in contact with the vocal folds, and is configured to provide an alert to the surgeon when contact is lost. In one embodiment, the NIM 120 is also configured to determine whether the electrodes 112 are in contact with muscle or tissue based on the received signals. In one embodiment, EMG tube 100 is configured to wirelessly communicate with the NIM 120 and the NIM 120 is configured to wirelessly monitor the electrodes 112. In form of this embodiment, the NIM 120 wirelessly transmits energy to the electrodes 112 and the electrodes 112 wirelessly transmit EMG signals to the NIM 120.

FIGS. 2A-2C illustrate different side views of tube 110. In particular, FIG. 2A is a posterior view of tube 110, FIG. 2B is a left side view of tube 110 and FIG. 2C is an anterior view of tube 110. As illustrated, the electrodes 112 include four electrodes 112A-112D, which are formed around a circumference of the electrode cuff 116 and extend in a longitudinal direction of the tube 110. In one embodiment, the electrodes 112 are formed of conductive ink applied to cuff 116 by tracing or printing a conductive ink on the cuff 116. Conductive inks are available in a variety of flowable material choices such as silver, carbon, gold, platinum, palladium, silver, tungsten and silver titanium. Conductive inks can be deposited onto cuff 116 using various known techniques such as pad printing, screen printing, ink jet dispensing, digital printing, micropen dispensing, painting, vapor deposition and plasma sputtering. Conductive ink electrodes 112 can be used both for stimulation and recording purposes in nerve monitoring applications.

Electrodes 112A and 112B are positioned on a posterior side of the tube 110 and are also referred to herein as posterior electrodes 112A and 112B. Electrodes 112C and 112D are positioned entirely on an anterior side of the tube 110 and are also referred to as anterior electrodes 112C and 112D. Each of the electrodes 112A-112D is coupled to a respective conductive trace 114A-114D. Traces 114A-114D are positioned in an insulated region 128 of tube 110. Posterior electrodes 112A and 112B are positioned in an exposed (uninsulated) region 126A of tube 110. Anterior electrodes 112C and 112D are positioned in an exposed (uninsulated) region 126B of tube 110.

In one embodiment, each of the electrodes 112A-112B has a length of about 1.875 inches and extends laterally around a circumference of the cuff 116 for a distance corresponding to an angle of about 60 degrees. Additionally, the electrodes 112A-112D are laterally spaced apart around the circumference of the cuff 116 by a distance corresponding to an angle of about 30 degrees. The posterior electrodes 112A and 112B are longitudinally offset or displaced from the anterior electrodes 112C and 112D. Due to this positioning, the posterior electrodes 112A and 112B are positioned to cover a greater length of cuff 116 than the anterior electrodes 112C and 112D.

Cuff 116 includes an overlap region 130 where a proximal portion of the posterior electrodes 112A and 112B longitudinally overlap the distal portion of the anterior electrodes 112C and 112D. The electrodes 112 do not physically overlap each other since they are laterally offset from each other. In one embodiment, the overlap region 130 is at least 0.1 inches long and the overall length from a proximal end of the anterior electrodes 112C and 112D to a distal end of the posterior electrodes 112A and 112B is approximately 2.5 inches. Tube 110 is configured to be positioned such that the vocal folds of a patient are positioned in the overlap region 130. Thus, the configuration of the electrodes 112 above the vocal folds is different than the configuration below the vocal folds. As such, the posterior electrodes 112A and 112B are configured to be positioned primarily below the vocal folds and the anterior electrodes 112C and 112D are configured to be positioned primarily above the vocal folds. In one embodiment, electrodes 112A and 112D are used for a first EMG channel and electrodes 112B and 112C are used for a second EMG channel.

In an alternate embodiment, all four surface printed electrodes, 112A-112D are equal in length. This arrangement allows tube 110 to be placed within a patient independent of rotational alignment of the electrodes 112A-112D with respect to the trachea of the patient.

With reference to FIG. 2C, cuffs 114 and 116 are sized so as to both provide suitable sealing between the trachea and anchoring cuff 114 yet provide suitable compliance of electrode cuff 116 in contact with the vocal folds of a patient when inflated by pressurized fluid provided within conduit 106. Upon inflation, the anchoring cuff 114 has a larger diameter D1 than a diameter D2 of electrode cuff 116. In some embodiments, the diameter D2 is selected to be approximately half the diameter D1. In one example, D1 is about 20 millimeters, whereas D2 is about 9 millimeters. In yet a further embodiment, D1 is approximately 27 millimeters, whereas D2 is approximately 14 millimeters. Moreover, a length L1 of the cuff 116 is selected to be greater than a length L2 for cuff 114. In one embodiment, the L1 is approximately 1.875 inches. In another embodiment, L1 is in a range from approximately 1.5 inches to 2.5 inches. In a further embodiment, a ratio of D1:L1 is selected to be in a range from approximately 15:100 to 30:100.

Furthermore, a compliance for cuffs 114 and 116 is selected so as to prevent trauma due to cuff 116 contacting the vocal folds of the patient. The compliance of cuffs 114 and 116 is proportional to a thickness (i.e., distance from an outer surface of material forming the cuff to an inner surface of the material) of the cuffs 114 and 116. In one embodiment, the cuff 116 is formed of a semi-compliant balloon. The semi-compliant balloon will increase in diameter about 10 to 20 percent from a nominal pressure to a rated burst pressure for the balloon. In a further embodiment, cuff 116 is formed of a compliant balloon such that the balloon will increase in diameter from 20 to 200 percent from a nominal pressure to a rated burst pressure of the balloon. In a further embodiment, the cuff 116 is formed of a compliant material that has equal compliance with a material selected for cuff 114. In one embodiment, cuff 114 has a compliance defined as increasing in diameter about 10 to 20 percent from a nominal pressure to a rated burst pressure for the cuff 114. In an alternative embodiment, cuff 114 has a compliance defined as increasing in diameter about 20 to 200 percent from a nominal pressure to a rated burst pressure for the cuff 114.

According to Laplace's law, tension in a wall increases with an increasing vessel radius. With this in mind, thickness of material and diameter for cuffs 114 and 116 can be selected as desired to reduce wall tension exhibited by electrode cuff 116 while providing sufficient contact between the electrodes 112A-112D and vocal folds. In selecting cuffs 114 and 116 to have equal thickness, the compliance of the cuffs 114 and 116 is equal. By selecting cuff 114 to have a larger diameter than cuff 116, tension exerted by cuff 116 will be less than that exerted by cuff 114. Thus, cuff 116 having a smaller radius will exhibit lower wall tension upon inflation than cuff 114. It will also be appreciated that a shape of cuffs 114 and 116 can be selected as desired. For example, also according to Laplace's Law, a spherical shaped cuff will exhibit less wall tension than a cylindrical shaped cuff.

Inflation conduit 106 is schematically illustrated in phantom in FIG. 2C, extending from a connector 150 and along the length of tube 110 to an electrode cuff opening 152 and continuing in extension to a anchoring cuff opening 154. Due to relative compliance of the cuffs 114 and 116, cuff 114 is configured to fluidly seal the trachea of a patient when positioned, whereas electrode cuff 116 inflates to contact the vocal folds of the patient so as to prevent trauma from occurring due to contact between the cuff 116 and the vocal folds.

Figure 3:
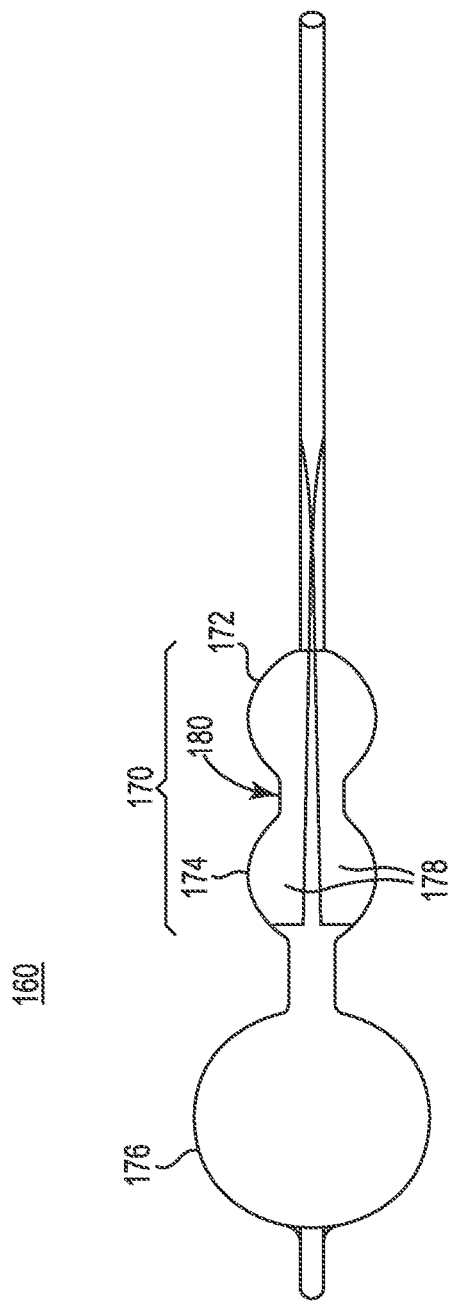
FIG. 3 is a side view of an alternative tube.

In a further embodiment, as illustrated in FIG. 3, a tube 160 includes an electrode cuff 170 formed of a dual chambered balloon having a first balloon 172 and a second balloon 174, while an anchoring cuff 176 is positioned distal the electrode cuff 170. Tube 160 is similar in structure to tube 110 discussed above, with cuff 170 being of a different shape than cuff 116. A plurality of printed surface electrodes 178 are applied to the cuff 170 and in particular to both balloons 172 and 174. In one embodiment, a narrow waist portion 180 is formed between the balloons 172 and 174, providing a recess to receive vocal folds of a patient in operation.

Although the present disclosure has been described with reference to preferred embodiments, workers skilled in the art will recognize that changes can be made in form and detail without departing from the spirit and scope of the present disclosure.

What is claimed is:

1. An apparatus for monitoring EMG signals of a patient, comprising:
   an endotracheal tube;
   a conduit extending along the endotracheal tube;
   a first cuff having an exterior surface defining a first diameter and fluidly coupled to the conduit, the first cuff exhibiting a first compliance such that the first diameter expands to a first distance when pressurized fluid is within the interior conduit;
   a second cuff having an exterior surface defining a second diameter, positioned distal the first cuff and fluidly coupled to the conduit, the second cuff exhibiting a second compliance equal to the first compliance and defined such that the second diameter expands to a second distance greater than the first distance when pressurized fluid is within the conduit, wherein upon inflation of the first cuff and the second cuff from fluid provided in the conduit, the first cuff exhibits a first wall tension on the exterior surface thereof and the second cuff exhibits a second wall tension on the exterior surface thereof, the first tension being less than the second tension; and conductive ink electrodes formed on the exterior surface of the first cuff.

2. The apparatus of claim 1, wherein the first distance is approximately one-half the second distance.

3. The apparatus of claim 1, wherein the first cuff defines a first length and the second cuff defines a second length less than the first length.

4. The apparatus of claim 1, wherein the conductive ink electrodes include four spaced apart electrodes positioned about a circumference of the exterior surface of the first cuff.

5. The apparatus of claim 1, wherein the first cuff further defines a first length and wherein a range of a ratio of the first distance to the first length is approximately 15:100 to 30:100.

6. The apparatus of claim 1, wherein the first compliance is defined such that the first diameter increases at least 10% from a nominal pressure to a rated burst pressure of the first cuff.

7. The apparatus of claim 1, wherein the first compliance is defined such that the first distance increases at least 20% from a nominal pressure to a rated burst pressure of the first cuff.

8. The apparatus of claim 1, wherein the electrodes are configured to record a vocal fold response and deliver stimulation to vocal folds of the patient.

9. The apparatus of claim 1, wherein the first cuff is formed of a first balloon and a second balloon having a waist portion disposed between the first and second balloons.

10. A method of operating an apparatus used in monitoring EMG signals of a patient, comprising:
providing a tube having a conduit extending along the tube;
providing an electrode cuff having an exterior surface defining an electrode cuff diameter and an electrode cuff compliance;
positioning conductive ink electrodes on the exterior surface of the electrode cuff;
providing a anchoring cuff having an exterior surface defining a anchoring cuff diameter and a anchoring cuff compliance, the anchoring cuff compliance being equal to the electrode cuff compliance; and
providing pressurized fluid through the conduit to inflate the electrode cuff and the anchoring cuff such that the electrode cuff diameter is less than the anchoring cuff diameter, wherein upon inflation of the electrode cuff and the anchoring cuff from fluid provided in the conduit, the electrode cuff exhibits a first wall tension on the exterior surface thereof and the anchoring cuff exhibits a second wall tension on the exterior surface thereof, the first tension being less than the second tension.

11. The method of claim 10, wherein upon inflation of the electrode cuff and the anchoring cuff, the electrode cuff diameter is approximately one-half the anchoring cuff diameter.

12. The method of claim 10, wherein the electrode cuff defines a first length and the anchoring cuff defines a second length less than the first length.

13. The method of claim 10, wherein the conductive ink electrodes include four spaced apart electrodes positioned about a circumference of the exterior surface of the electrode cuff.

14. The method of claim 10, wherein the electrode cuff further defines a first length and wherein a range of a ratio of the electrode cuff diameter to the first length is approximately 15:100 to 30:100.

15. The method of claim 10, wherein the electrode cuff compliance is defined such that the electrode cuff diameter increases at least 10% from a nominal pressure to a rated burst pressure of the electrode cuff.

16. The method of claim 10, wherein the electrode cuff compliance is defined such that the electrode cuff diameter increases at least 20% from a nominal pressure to a rated burst pressure of the first cuff.

17. The method of claim 10, further comprising:
recording a vocal fold response from the patient using the electrodes.

18. The method of claim 10, further comprising:
delivering stimulation to vocal folds of the patient using the electrodes.

19. The method of claim 10, wherein the electrode cuff is formed of a first balloon and a second balloon having a waist portion between the first and second balloons, the waist portion being positioned to receive the vocal folds.

* * * * *